United States Patent [19]

Danna et al.

[11] 4,199,322

[45] Apr. 22, 1980

[54] ANTIBACTERIAL TEXTILE FINISHES UTILIZING ZINC ACETATE AND HYDROGEN PEROXIDE

[75] Inventors: Gary F. Danna, New Orleans, La.; Tyrone L. Vigo, Knoxville, Tenn.; Clark M. Welch, Metairie, La.

[73] Assignee: The United States of America as represented by the Secretary of Agriculture, Washington, D.C.

[21] Appl. No.: 974,171

[22] Filed: Dec. 28, 1978

Related U.S. Application Data

[62] Division of Ser. No. 934,288, Aug. 17, 1978, Pat. No. 4,172,841.

[51] Int. Cl.$^2$ .................. D06M 13/34; B05D 3/02
[52] U.S. Cl. ........................... 8/186; 427/394; 427/395; 427/396; 252/8.6; 162/161
[58] Field of Search ............ 427/395, 396, 394; 8/186; 252/8.6

[56] References Cited

U.S. PATENT DOCUMENTS

| | | | |
|---|---|---|---|
| 2,833,669 | 5/1958 | Ziegler | 427/395 |
| 3,082,118 | 3/1963 | Shaw et al. | 8/186 |
| 3,148,937 | 9/1964 | Ross et al. | 8/186 |
| 3,446,656 | 5/1969 | Connor | 427/396 |
| 3,594,113 | 7/1971 | Lifland et al. | 8/186 |
| 3,709,716 | 1/1973 | Liggett | 427/396 |

*Primary Examiner*—Donald E. Czaja
*Assistant Examiner*—Maria S. Tungol
*Attorney, Agent, or Firm*—M. Howard Silverstein; David G. McConnell; Raymond C. Von Bodungen

[57] ABSTRACT

The preparation of bacteriostatic, water-insoluble peroxide-containing complexes of zinc acetate, by reaction of zinc acetate with hydrogen peroxide in the presence of acetic acid, is disclosed. A process for in situ formation and deposition of these complexes on cellulosic and polyester textiles is described. The textile finishes so produced inhibit the growth and spreading of odor- and infection-producing gram-positive and gram-negative bacteria on the treated textiles. The antibacterial activity of the finished textiles is durable to repeated launderings.

15 Claims, No Drawings

ANTIBACTERIAL TEXTILE FINISHES UTILIZING ZINC ACETATE AND HYDROGEN PEROXIDE

This is a division of application Ser. No. 934,288, filed Aug. 17, 1978, now U.S. Pat. No. 4,172,841.

BACKGROUND OF THE INVENTION

1. Field of the Invention

This invention relates to a new method of imparting antibacterial activity to textiles made of cellulosic fibers, polyester fibers or blends of cellulose with polyester.

2. Description of the Prior Art

Although many types of antibacterial agents have previously been applied to cellulosic and non-cellulosic textiles, the resulting textile materials have generally been deficient in certain properties essential to successful commercial use. Seldom have the products possessed a combination of strong activity against undesirable species of bacteria, together with the necessary durability to repeated laundering. In many instances, previous antibacterial agents have produced undesired physiological side effects on contact with human skin or exposed tissue, or they adversely affected the color, suppleness, softness, and absorbency of the textile. In addition, such agents have usually been expensive to manufacture. Various types of antibacterials previously studied for textile applications have been described by Gagliardi, *American Dyestuff Reporter* 51 [2] P49–P58 (1962).

It has been known for many years that hydrogen peroxide is a safe and effective topical and oral antiseptic and disinfectant when used in dilute aqueous solution, and it can be used to cleanse open wounds. By itself, it has no substantivity for cellulosic or polyester materials, and is removed in a single washing from yarns or fabrics to which it is applied.

Recently, however, hydrogen peroxide has been shown to form colorless, water-insoluble complexes with zirconyl acetate, and these complexes can be formed in situ as durable deposits on cellulosic textiles, thereby imparting considerable antibacterial activity (Vigo et al, *Textile Chemist and Colorist* 9 [4] 77–80 (1977); Welch et al, co-pending U.S. patent application, Ser. No. 787,177 filed Apr. 12, 1977). The antibacterial activity of the treated textiles appears to be due to a slow, controlled release of hydrogen peroxide as the effective antibacterial agent. This peroxide release at the textile surface appears to result from the slow reaction of zirconyl acetate-hydrogen peroxide complexes with the regain moisture present in cellulosic fibers of the textile at equilibrium with air at ordinary humidity. In order to obtain even a peroxide content of 0.30%–0.35% in treated fabric, a very high concentration of zirconyl acetate had to be applied, and this led to fabric weight gains of 12%–16%. Such high fabric loadings increased the stiffness, caused a somewhat harsh feel, and decreased the wettability and absorbency of the fabric to an undesirable extent.

It is also well known that a simple, insoluble peroxide of zinc having the formula $ZnO_2$ can be prepared by adding solid zinc oxide to a solution of hydrogen peroxide containing small concentrations of mineral acid. The product forms as a granular solid (Wood and Clennett, U.S. Pat. No. 2,563,442). A similar product has been made by treating the basic carbonate of zinc in solid form with concentrated hydrogen peroxide (Laporte Chemicals Ltd., French Pat. No. 1,524,638).

SUMMARY OF THE INVENTION

A process for imparting antibacterial activity to cellulosic and polyester textiles is disclosed wherein the textile is treated with an aqueous solution which contains 1%–30% by weight of zinc acetate and 1%–30% of hydrogen peroxide, and which, at zinc acetate concentrations of 5% or greater, also contains 1%–25% of acetic acid, the textile subsequently being heated to drive off water and acetic acid, thereby converting the water-soluble reagents to insoluble peroxide complexes of zinc acetate deposited on the textile.

The new treatment is applicable to unfinished textiles and also to cellulosic textiles having a durable press finish. The new treatment inhibits the growth and spreading of odor- and infection-producing bacteria on the textile, and the antibacterial activity imparted is durable to repeated laundering.

The present invention also includes the preparation of the water-insoluble peroxide complexes of zinc acetate in the absence of a cellulosic or polyester substrate, as a means of obtaining antibacterial dusting powders.

DESCRIPTION OF THE PREFERRED EMBODIMENTS

The processes of the present invention are based on the discovery that zinc acetate forms hitherto unknown water-insoluble complexes upon reaction with hydrogen peroxide. These complexes are more stable and contain a much higher percentage of bound peroxide, than is the case for zirconyl acetate-hydrogen peroxide complexes of the prior art. Also, the antibacterial activity of the peroxide available in the zinc complexes appears to be considerably augmented by the presence of the zinc ions, which in themselves are known to possess considerable antibacterial activity (Rowland et al, *American Dyestuff Reporter* 65 [7] 46–47 (1976); Gagliardi, loc. cit). The complexes are also more active on olyester textiles than is the case with the zirconyl complexes.

However, no method is known for impregnation of textiles with this insoluble compound to give a uniform, durable, non-dusting film around the fibers of the textile. The zinc acetate-hydrogen peroxide reaction products of the present invention contain a significant proportion of acetyl groups as indicated by chemical analysis, and differ in this respect from the simple zinc peroxide known to the prior art. Moreover, the prior art offers no means of preparing a homogeneous solution which can be applied to textile materials, and from which insoluble complexes containing both zinc and peroxide can subsequently be deposited on the surface of a textile.

In the processes of this invention, the zinc acetate used may be either the anhydrous salt or the more widely available dihydrate having the formula $Zn(OOCCH_3)_2 \cdot 2H_2O$, but in the description that follows, all percentages are by weight and refer to the anhydrous compound, except where specifically stated otherwise.

The processes of this invention are based on the discovery that zinc acetate reacts with hydrogen peroxide in aqueous media to form solid, colorless, water-insoluble complexes whose elemental analyses correspond to the structure

where x has values in the range of 9–16, and y has values in the range of 1–7. The value of x and y vary with the proportions of zinc acetate and hydrogen peroxide used in carrying out the reaction. The analyses indicate that these water-insoluble products are polymeric complexes derived from three simple compounds; namely, zinc peroxide, zinc oxide and zinc acetate.

The reaction to form these complexes proceeds to completion only if the water present as solvent, and the acetic acid formed as co-product, are removed by evaporation. The evaporation can be hastened by heating the mixture at atmospheric pressure or under partial vacuum, the pressure being in the range of 0.1–1 atmosphere.

Since hydrogen peroxide is much less expensive mole for mole than zinc acetate, it is preferable to carry out the reaction in the presence of excess hydrogen peroxide, especially since some hydrogen peroxide may be lost through volatilization during the evaporation step. At zinc acetate concentrations of less than 5% (or less than 6% calculated as as zinc acetate dihydrate) the mixing of zinc acetate, hydrogen peroxide and water yields slightly hazy but still reasonably uniform and usable solutions. At higher concentrations of zinc acetate, however, precipitates of peroxide complexes appear. This precipitation can be prevented and even reversed by the addition of 0.2–3.0 parts by weight of acetic acid per part of zinc acetate, to give an acetic acid concentration of 1%–25%. The addition of acetic acid is essential when it is desired to apply the peroxide complexes as a concentrated uniform, homogeneous solution to textile materials and can also be advantageous in preparing batches of the solid complexes themselves, since a non-uniform product results when the composition of the initially precipitated solids differs from that of solids subsequently formed as evaporation proceeds. The use of acetic acid for this purpose has the advantage that this acid is volatile and readily removed by vaporization along with the water present. Evaporation to dryness converts the water-soluble reagents to the desired water-insoluble peroxide complexes.

In preparing the solid, water-insoluble peroxide complexes, any order of addition and mixing of zinc acetate, hydrogen peroxide, acetic acid and water is operable, but for preparation of a solution for application to textiles, it is somewhat preferable to mix zinc acetate with an excess of 25%–50% aqueous hydrogen peroxide, subsequently adding glacial acetic acid and finally adding water to obtain a homogeneous solution. This order of addition resulted in somewhat greater retention of antibacterial activity of the treated textile after repeated laundering.

Batches of the water-insoluble peroxide complexes of zinc acetate may be prepared using a wide range of reagent proportions and concentrations, the only limitations being the solubility limit for zinc acetate or its dihydrate, and practical considerations of economy, which make it preferable to use more than one mole of hydrogen peroxide per mole of zinc acetate. The aqueous reaction mixtures may contain 1%–30% zinc acetate, and preferably from 1.5 to 10.0 moles hydrogen peroxide per mole of zinc acetate or its dihydrate, to give a hydrogen peroxide concentration of 1%–50% in the mixture. Addition of 1%–25% acetic acid is carried out to give a clear solution. On evaporation of the mixture, a colloidal suspension is often produced which is difficult to filter. Therefore the mixture is preferably evaporated to complete dryness to coagulate the colloidal particles. The solid residue is then washed with water to remove any soluble impurities or unreacted starting materials, and the water-insoluble peroxide complexes are isolated by filtration and drying. The temperatures used in the evaporation and drying steps are preferably in the range of 50°–120° C. to avoid possible decomposition and loss of peroxide complexes that might take place at higher temperatures, although these complexes are fairly stable to temperatures as high as 160° C. for short intervals, not exceeding 5 minutes.

The above findings have been used to develop the process of the present invention for the preparation of bacteriostatic textiles. This process comprises the following steps:

(a) immersion of a cellulosic or polyester textile in an aqueous treating solution which contains about from 1% to 30% zinc acetate and from 1% to 30% hydrogen peroxide in water, and which, at zinc acetate concentrations of 5% or greater, also contains from 1% to 25% acetic acid to prevent precipitation of peroxide complexes of zinc acetate, (b) removal of excess treating solution from the textile, (c) heating the textile at a temperature of from about 50° C. to 160° C. for from 0.5 minutes to 30 minutes in order to dry the textile and cause deposition of peroxide complexes of zinc acetate on the textile, the higher temperatures being used for the shorter times, (d) washing the textile with water to remove excess reagents, and (e) drying the treated textile at a temperature of 50° C. to 140° C. for from 0.5 minutes to 30 minutes.

In step (a) of the above textile finishing process, the preferred mole ratios of hydrogen peroxide to zinc acetate are 1.5–10.0 as already indicated for the preparation of the peroxide complexes themselves, but mole ratios outside this range are also operative. The maximum concentration of zinc acetate that can be used is fixed by the solubility of this compound in water at room temperature. The use of hydrogen peroxide at greater than a 30% concentration leads to excessive degradation and strength loss in cellulosic textiles. The presence of acetic acid in the treating solution is essential for bath homogeneity when the zinc acetate concentration equals or exceeds 5%, as already indicated. The preferred weight ratios of acetic acid to zinc acetate are in the range of 0.2–3.0 for the textile treatment as well as for the preparation of the complexes, but other ratios are operative. The preferred order of addition in preparing the treating solution is that of adding the acetic acid to a mixture of zinc acetate and 25%–50% aqueous hydrogen peroxide, and finally adding the water. However, this order is optional and examples of the inverse order of addition are included below. In carrying out step (a), the textile used may be roving, yarn or fabric regardless of whether spun, knit, or woven, or may be nonwoven sheets or webs. The textile may be made of cellulosic fibers, polyester fibers or blends of these.

Yarns and fabrics already finished with a durable press reagent such as dimethyloldihydroxyethyleneurea or dimethylolethyleneurea are likewise suitable for this process. In wetting the textile in the treating bath, ordinary textile equipment and methods suitable for batchwise or continuous passage of roving, yarns or fabrics through an aqueous solution may be used, at any speed permitting thorough and uniform wetting of the textile material. If a wetting agent is used to increase the rate and completeness of wetting, such an agent should be nonionic in order that the precipitation of zinc complexes in the treating bath may be avoided.

In step (b) the excess textile treating solution may be removed by ordinary mechanical methods such as by passing the textile between squeeze rolls, by centrifugation, or by draining.

In step (c), the purpose of heating the impregnated textile is to drive off water and acetic acid by volatilization, and to convert the water-soluble zinc acetate and hydrogen peroxide to water-insoluble peroxide complexes of zinc acetate deposited in the textile material in a form durable to removal by subsequent laundering. The peroxide complexes are stable to temperatures of 50° C.–120° C. for long periods of time, but at temperatures of 140°–160° C., the heating time should not exceed 5 minutes, and much shorter times often suffice. The heating may be carried out in an oven, preferably one having a forced draft of air directed at the surface of the textile and exhausting through a vent to remove fumes of acetic acid and water vapor.

Washing of the treated textile, step (d), may be done with either hot or cold water. The peroxide complexes of zinc acetate are stable, insoluble, and durable to the mechanical agitation, spraying and rubbing that occurs in washing machines or in large scale continuous or batchwise textile washing equipment.

Final drying, step (e), can be carried out by any ordinary means such as oven drying, line drying, or tumble drying in a mechanical clothes dryer. High temperatures, in excess of 140° C. for long periods, should be avoided to ensure against thermal decomposition of the peroxide complexes in the textile finish. A drying temperature of 80°–120° C. for 1–5 minutes is particularly preferred.

In the following examples, all parts and percentages are by weight. Analyses for zinc were run by X-ray fluorescence. Analyses for peroxide (—O—O—) content in treated fabric were conducted iodometrically by a procedure similar to that of Wentz and Cates, Textile Research J. 45 691 (1975), as follows: 50 ml deionized water, 1 ml of 37% aqueous hydrochloric acid and 1 ml of saturated aqueous potassium iodide were added to the weighed fabric sample in a flask, and the mixture was heated on a steam cone for 10 min. followed by titration with standardized 0.1N sodium thiosulfate. The peroxide content of isolated zinc acetate-hydrogen peroxide complexes was similarly determined except that sufficient hydrochloric acid was added prior to titration to bring all the complex into aqueous solution.

Antibacterial activity of treated fabrics was determined qualitatively by the parallel streak test of the American Association of Textile Chemists and Colorists (AATCC Test Method 147-1976) with the gram-positive bacteria *Staphylococcus aureus*. Quantitative tests for antibacterial activity were run by the Quinn method (AATCC Test Method 100-1974; H. Quinn, *Applied Microbiology* 10 74–78 (1962)), using gram-positive *Staphylococcus epidermidis* and gram-negative *Klebsiella pneumoniae* bacteria. *Staphylococcus aureus* and *Klebsiella pneumoniae* produce infections in skin wounds, sores, boils, lesions, and abscesses, while *Staphylococcus epidermidis* acts on human perspiration to cause undesirable odors often referred to as "body odor".

Antifungal activity of treated fabric was determined by adapting the Quinn procedure already mentioned to the use of *Trichophyton mentagrophytes* as inoculant. This fungus is one of the principal causes of ringworm infections of the feet (so-called "athletes' foot"), hands, nails, body, scalp, and bearded regions of the face (S. Shadomy, H. J. Shadomy and G. E. Wagner, Chapter 13 of "Antifungal Compounds. Vol. I. Discovery, Development and Uses", M. R. Siegel and H. D. Sisler, editors, Marcel Dekker, Inc., 1977, pp. 442–444). The reduction in amount of fungus found in a treated fabric, relative to untreated control fabric, was determined by microscopical observation and expressed in graded terms: none, slight, moderate, substantial, and complete.

Wrinkle recovery of treated fabrics was measured by the recovery angle method of the American Association of Textile Chemists and Colorists (AATCC Test Method 66-1975). Durability of fabric finishes to laundering was determined in an agitator-type washing machine and tumble dryer of the type specified in AATCC Test Method 124-1975, using normal conditions for cotton (14 min. hot water wash, 30 min. high temperature drying) with the commercial AATCC standard detergent 124. The 80×80 desized, scoured, and bleached cotton printcloth used weighed 3.2 oz. per square yard. Polyester and blend fabrics were similar in having printcloth construction.

EXAMPLE 1

Preparation of Zinc Acetate-Hydrogen Peroxide Complexes (A) To 40.0 parts by weight of zinc acetate dihydrate in a beaker was added with stirring 125 parts of 30% aqueous hydrogen peroxide, 34.6 parts glacial acetic acid, and 52.8 parts of water. The resulting solution was transferred to a round bottom flask which was then attached to a rotary evaporator fitted with a water bath and connected to a water aspirator. The solution was evaporated under reduced pressure for 4 hrs. at 70° C., and thereafter for 2 hrs. at 50° C. The gummy residue was cooled to 25° C., transferred to an evaporating dish and dried in an oven to 85° C. for 135 min. The light yellow solid was broken up, powdered and slurried with 200 parts water. The slurry was filtered by suction, was washed four times with 25 parts water and was filtered after each washing. The white solid was dried at 85° C. for 15 min. By chemical analysis, it was found to contain 22.3% peroxide, 65.7% zinc, and 2.40% carbon. All the carbon was present as acetyl groups, as indicated by a measured acetyl content of 5.3%. The analyses correspond to a polymer of the formula

(B) The preparation of the complex was carried out by a procedure similar to (A) except that quantity of glacial acetic acid used in making up the initial zinc acetate dihydrate-hydrogen peroxide-acetic acid solution in water was only 21.0 parts by weight. The mixture was mechanically shaken for 30 min in a stoppered flask, whereupon a clear solution was obtained. The product was a white solid analyzing 22.5% peroxide, 65.5% zinc and 3.09% carbon. All the carbon was present as acetyl groups, as indicated by a measured acetyl content of 5.9%. The analyses correspond to a polymer of the formula

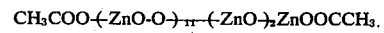

EXAMPLE 2

Application of Zinc Acetate-Hydrogen Peroxide Solution to Cotton at High Acetic Acid Concentration To 40.0 parts by weight of zinc acetate dihydrate in a beaker were added with stirring 125 parts of 30% hydrogen peroxide, 34.6 parts of glacial acetic acid and 52.8 parts of water, to give an aqueous solution similar in composition to the solution of Example 1-A, and containing 15.8% zinc acetate dihydrate, 14.9% hydrogen peroxide and 13.7% acetic acid. Desized, scoured and bleached 80×80 cotton printcloth was immersed in the solution until thoroughly wet, and was then passed between squeeze rolls of a wringer, with the roll pressure adjusted to give a wet pickup of 108%. The fabric was heat-cured in a forced-draft oven for 5 min. at 85° C. It was then washed for 15 min. in hot running water at 60° C., and oven-dried for 5 min. at 85° C.

The fabric had a weight gain of 4.2%, and contained 0.74% bound peroxide, as well as 2.70% zinc. Samples of the treated fabric were given repeated launderings in an automatic clothes washer and a tumble dryer. The fabric samples were then analyzed for zinc and peroxide content, and tested by means of the AATCC parallel streak test for antibacterial activity using *Staphylococcus aureus* as the inoculant. The results of these tests are shown in Table I.

Table I

| Fabric | Number of Launderings | % Zn | % Peroxide | Bacterial Undergrowth | Width of Inhibition Zone | Test Rating |
|---|---|---|---|---|---|---|
| treated | 0 | 2.7 | 0.74 | None | 3.0 mm[a] | passed |
|  | 5 |  |  | None | 2.5 | passed |
|  | 20 | 0.6 | 0.23 | None | 0 | passed |
|  | 35 |  |  | None | 0 | passed |
|  | 50 | 0.2 | 0.12 | Very slight | 0 | passed |
| untreated | 0 | 0.0 | 0.02 | Extensive | 0 | failed |

[a]Average of duplicate experiments

Samples of treated and laundered fabrics were also subjected to the Quinn test for antibacterial activity using *Staphylococcus aureus*, *Staphylococcus epidermidis* and *Klebsiella pneumoniae* as inoculants. The inoculated fabrics were incubated, and bacterial colonies were afterwards counted under a microscope. The percent decrease in colony count relative to untreated, unlaundered fabric was calculated. The results are shown in Table II.

Table II

| Number of Launderings | Percent Decrease in Colony Count | | |
|---|---|---|---|
|  | S. aureus | S. epidermidis | K. pneumoniae |
| 0 | 100 | 100 | 100 |
| 10 | 100 |  | 71 |
| 20 |  | 100 |  |
| 25 | 100 |  | 16 |
| 50 | 100 | 100 | 12 |

The test results show that the application to cotton fabric of the above zinc acetate-hydrogen peroxide-acetic acid formulation made the fabric completely resistant to the growth of these three species of bacteria on the fabric surface. The treated fabric retained its activity against two species of bacteria even after 50 launderings and tumble-dryings.

Inoculation and incubation of treated fabrics with *Trichophyton mentagrophytes*, a fungus active in causing ringworm of the feet and hands, was carried out in a manner analogous to the Quinn test, above. Treated, unlaundered fabric showed substantially decreased fungal growth as compared to untreated fabric, and even after twenty laundering cycles, the treated fabric still showed moderately decreased fungal growth.

EXAMPLE 3

Effect of Curing Temperature Used in Fabric Treatment

Fabric treatment was carried out using the procedure and conditions of Example 2, except for the temperature used in the heat-curing step. The properties of the treated fabrics are shown in Table III, in terms of zinc and peroxide content, and activity against *Staphylococcus aureus* in the parallel streak test.

Table III

| Cure Temperature | Fabric Weight Gain | % Zn | % Peroxide | Bacterial Undergrowth | Width of Inhibition Zone | Test Rating[c] |
|---|---|---|---|---|---|---|
| 23° C.[a] | 3.3% | 1.68 | 0.48 | None | 2.0 mm | passed |
| 85[b] | 4.2 | 2.70 | 0.74 | None | 3.0 | passed |
| 120 | 4.0 | 3.26 | 0.79 | None | 2.0 | passed |
| 140 | 3.9 | 2.80 | 0.80 | None | 2.5 | passed |
| 160 | 3.6 | 3.41 | 0.79 | None | 4.0 | passed |

[a]Cure time: 24 hrs in this run only, 5 min. in all other runs.
[b]Same duplicate runs as in Example 2, Table I.
[c]For behavior of untreated fabric, see Table I.

The data show that a wide range of curing temperatures are suitable for the process of binding zinc ions and peroxide to cotton to impart antibacterial activity to cotton fabric.

EXAMPLE 4

Application of Zinc Acetate-Hydrogen Peroxide Solution to Cotton at Medium Acetic Acid Concentration To 40.0 parts by weight of zinc acetate dihydrate in a flask were added with agitation 125 parts of 30% hydrogen peroxide, 21.0 parts of glacial acetic acid, and 52.8 parts water. The flask was then stoppered and mechanically shaken for 30 min. to give a clear solution like that of Example 1-B. The solution was applied to 80×80 cotton printcloth using the procedure and conditions of Example 2. The gain in weight of the fabric was 6.5%. The treated fabric was analyzed for zinc and peroxide content. Subsequently samples of the treated fabric were repeatedly laundered and tumble dried, and tested for activity against *Staphylococcus aureus* by the parallel streak method. The results are shown in Table IV.

Table IV

| Number of Launderings | % Zn | % Peroxide | Bacterial Undergrowth | Width of Inhibition Zone[a] | Test Rating[b] |
|---|---|---|---|---|---|
| 0 | 2.8 | 0.93 | None | 3.0 mm | passed |
| 5 |  |  | None | 1.8 | passed |
| 20 |  |  | None | 0.3 | passed |
| 35 |  |  | None | 0 | passed |
| 50 | 0.72 | 0.27 | Very slight | 0 | passed |

[a]Average of duplicate experiments.
[b]For behavior of untreated fabric, see Table I.

Comparison of Table IV with Table I shows that decreasing the acetic acid concentration in the treating formulation resulted in an increase in the peroxide content obtained in the treated fabric, both before and after 50 launderings. Untreated fabric developed extensive undergrowth when inoculated with *Staphylococcus aureus*, and failed the parallel streak test, whereas treated fabric showed no undergrowth and passed the test even after many launderings.

Samples of fabric treated at medium acetic acid concentration were subjected, after laundering, to the Quinn test for antibacterial activity. *Staphylococcus aureus, Staphylococcus epidermidis,* and *Klebsiella pneumoniae* were used as inoculants. The decrease in colony count relative to untreated unlaundered fabric was determined, as shown in Table V.

Table V

| Number of | Percent Decrease in Colony Count | | |
|---|---|---|---|
| Launderings | S. aureus | S. epidermidis | K. pneumoniae |
| 0 | 100 | 100 | 100 |
| 10 | 100 | | 62 |
| 20 | | 100 | |
| 25 | 100 | | 8 |
| 50 | 100 | 100 | 5 |

EXAMPLE 5

Effect of Order of Addition of Reagents in Preparing the Fabric Treating Solution To 52.8 parts by weight of water in a flask was added 125 parts of 30% hydrogen peroxide, 21.0 parts glacial acetic acid, and 40.0 parts zinc acetate dihydrate. The flask was then stoppered and mechanically shaken for 30 min. The resulting solution was applied to 80×80 cotton printcloth using the procedure and conditions of Example 2. The treated fabric was subjected to the parallel streak test for activity against *Staphylococcus aureus* before and after repeated launderings. The results appear in Table VI.

Table VI

| Number of Launderings | % Zn | % Peroxide | Bacterial Undergrowth | Width of Inhibition Zone | Test Rating[a] |
|---|---|---|---|---|---|
| 0 | 3.07 | 1.04 | None | 2.0 mm | passed |
| 5 | 2.39 | 0.90 | None | 0 | passed |
| 20 | 1.20 | 0.56 | Very slight | 0 | passed |
| 35 | 0.96 | 0.34 | Very slight | 0 | passed |
| 50 | 0.77 | 0.20 | Very slight | 0 | passed |

[a]For behavior of untreated fabric, see Table I.

Untreated, unlaundered fabric showed extensive bacterial undergrowth after inoculation with *Staphylococcus aureus* and failed the parallel streak test. Treated fabric showed no bacterial undergrowth when tested before or after 5 launderings, and showed only slight undergrowth when inoculated after 20–50 launderings. A comparison of Table VI with Table IV indicates, however, that the fabric treatment of Example 4 was more effective after 5–35 launderings than was the treatment of the present Example. The only difference in procedure was the order of addition of reagents in making up and treating solution. The order of addition used in Example IV is therefore preferred.

Samples of the treated fabric of the present example were also subjected to the Quinn test using *Staphylococcus epidermidis* as the inoculant. The treated fabric showed a 100% decrease in bacterial colony count relative to untreated, unlaundered fabric, and this decrease was maintained through 0, 20, and 50 laundering cycles.

EXAMPLE 6

Application of Zinc Acetate-Hydrogen Peroxide Solution to Cotton at Low Acetic Acid Concentration To 52.8 parts by weight of water in a flask was added 125 parts of 30% aqueous hydrogen peroxide, 10.5 parts glacial acetic acid and 40.0 parts zinc acetate dihydrate. The flask was then stoppered and mechanically shaken for 15 min. The resulting solution was applied to 80×80 cotton printcloth using the procedure and conditions of Example 2. The fabric weight gain was 8.5%. Zinc and peroxide content, and antibacterial activity against *Staphylococcus aureus* by the parallel streak test, are shown in Table VII.

Table VII

| Number of Launderings | % Zn | % Peroxide | Bacterial Undergrowth | Width of Inhibition Zone | Test Rating[a] |
|---|---|---|---|---|---|
| 0 | 3.38 | 1.22 | None | 8.0 mm | passed |
| 5 | 2.46 | 0.80 | None | 1.0 | passed |
| 20 | 1.10 | 0.50 | None | 0 | passed |
| 35 | 0.72 | 0.35 | None | 0 | passed |
| 50 | 0.65 | 0.23 | None | 0 | passed |

[a]For behavior of untreated fabric, see Table I.

Untreated, unlaundered fabric failed the parallel streak test with *Staphylococcus aureus,* showing extensive undergrowth after inoculation and incubation. Comparison of Table VII with Table I again shows that decreasing the acetic acid concentration in the treating formulation results in an increase in the amount of peroxide bound to the fabric. The zinc content obtained also was increased.

Samples of the treated fabric were subjected to the Quinn test for antibacterial activity, using *Staphylococcus epidermidis* as the inoculant. Treated fabric gave a 100% decrease in bacterial colony count relative to the count for untreated, unlaundered fabric, and this decrease was maintained through 20, 35 and 50 laundering cycles.

EXAMPLE 7

Effect of Varying Reagent Ratios in Preparing the Fabric Treating Solution

A number of samples of 80×80 cotton printcloth were treated using the procedure and conditions of Example 2 except that the relative proportions of the zinc acetate, hydrogen peroxide and acetic acid in the treating solution were varied. The properties of fabric samples so treated are shown in Table VIII in terms of percent zinc and peroxide bound to the fabric, and antibacterial activity of the fabric toward *Staphylococcus aureus* in the parallel streak test.

Table VIII

| Treating Bath | | | Fabric Weight Gain | % Zn | % Peroxide | Baterial Undergrowth | Inhibition Zone | Test Rating |
|---|---|---|---|---|---|---|---|---|
| Zn(OAc)$_2$[a] | H$_2$O$_2$ | HOAc | | | | | | |
| 16.0%[b] | 14.9% | 13.2% | 4.2% | 2.70 | 0.74 | None | 3.0 mm | passed |
| 16.0 | 7.5 | 13.2 | 3.3 | 0.81 | 0.34 | None | 3.0 | passed |
| 8.0 | 14.9 | 13.2 | 3.6 | 1.18 | 0.38 | None | 2.0 | passed |
| 8.0 | 17.3 | 13.2 | 3.1 | 1.39 | 0.44 | None | 2.0 | passed |
| 8.0 | 14.9 | 21.2 | 2.4 | 0.96 | 0.27 | None | 1.5 | passed |
| 5.0 | 3.0 | 1.0 | 0.9 | 0.23 | 0.07 | None | 0 | passed |

Table VIII-continued

| Treating Bath | | | Fabric Weight Gain | % Zn | % Peroxide | Baterial Undergrowth | Inhibition Zone | Test Rating |
|---|---|---|---|---|---|---|---|---|
| Zn(OAc)$_2$[a] | H$_2$O$_2$ | HOAc | | | | | | |
| 5.0 | 3.0 | 0 | 1.5 | 0.57 | 0.20 | None | 2.0 | passed |
| 5.0 | 0 | 0 | 0.8 | 0.20 | 0.02 | Extensive | 0 | failed |
| 0[c] | 0 | 0 | 0 | 0.02 | 0 | Extensive | 0 | failed |

[a]% Zinc acetate dihydrate.
[b]Same duplicate runs as in Example 2, Table I.
[c]Untreated fabric.

In those runs in which hydrogen peroxide was present in molar excess over the zinc acetate in the treating bath, the amount of hydrogen peroxide bound to the fabric was approximately proportional to the zinc acetate concentration used. This indicates the zinc acetate and hydrogen peroxide are bound together as a complex which is deposited on the cotton.

The data also show that when a zinc acetate dihydrate concentration as low as 5% is used, no acetic acid is required in the treating bath to solubilize the zinc acetate-hydrogen peroxide reaction product. Only a faint haziness was observed in this treating solution, whereas at zinc acetate dihydrate concentrations of 6% or higher, cloudiness and precipitation resulted if no acetic acid were added.

EXAMPLE 8

Post-Application of Zinc Acetate-Hydrogen Peroxide to Durable Press Cotton Fabric Cotton 80×80 printcloth which had been desized, scoured and bleached was treated with a standard durable press finishing agent, dimethyloldihydroxyethyleneurea (DMDHEU), in the following way: the fabric was immersed and thoroughly wet in an aqueous solution containing 11.0% DMDHEU together with 0.5% zinc nitrate hexahydrate which serves as a Lewis acid catalyst. The fabric was passed through a wringer adjusted to a squeeze roll pressure giving a wet pickup of 98%. The cloth was oven-dried at 85° C. for 5 min. and then oven-cured at 160° C. for 3 min. to produce cellulose crosslinking. The fabric was washed and then redried at 85° C. for 5 min. The fabric weight gain was 7.8%. The wrinkle recovery angle after the fabric was conditioned at standard humidity was 287° (sum of warp and fill values). Untreated fabric had a wrinkle recovery angle of 196°.

To this wrinkle resistant, durable press fabric was applied a treating solution containing 40.0 parts by weight of zinc acetate dihydrate, 125 parts of 30% aqueous hydrogen peroxide, the amount of glacial acetic acid specified in Table IX and 52.8 parts water. The fabric was immersed and thoroughly wet in the treating solution, and was passed through a wringer having squeeze rolls adjusted to give a wet pickup of 105%–120%. The fabric was heat-cured in a forced-draft oven for 5 min. at 85° C., was afterwards washed for 15 min. in hot running water at 60° C., and was oven-dried for 5 min. at 85° C. The zinc and peroxide content, and fabric performance in the parallel streak test with *Staphylococcus aureus,* are shown in Table IX.

Table XI

| Acetic Acid in Treating Bath[a] | Fabric Weight Gain[b] | % Zn | % Peroxide | Bacterial Undergrowth | Width of Inhibition Zone | Test Rating | WRA[c] |
|---|---|---|---|---|---|---|---|
| 34.6 parts | 9.5 | 3.0 | 0.90 | None | 5.0 mm | passed | 278° |
| 21.0 | 7.6 | 2.5 | 1.15 | None | 5.0 | passed | 277 |
| 10.5 | 9.4 | 2.5 | 1.24 | None | 3.0 | passed | 271 |

[a]Treating solution prepared as described in Examples 2, 4, and 6 respectively.
[b]Gain in weight during zinc acetate-H$_2$O$_2$-HOAc application.
[c]Wrinkle recovery angle (warp plus fill).

In the absence of the zinc acetate-hydrogen peroxide post-application, the DMDHEU-treated printcloth failed to give a zone of bacterial inhibition in the parallel streak test. The results show that the processes of the present invention can be applied as readily to durable press cotton fabrics as to untreated cotton. Fabric given the post-application also gave 100% reduction of the *Staphylococcus epidermidis* colony count as observed in the Quinn test.

EXAMPLE 9

Application of Zinc Acetate-Hydrogen Peroxide to Polyester and Cotton-Polyester Blends The procedure and conditions of Example 2 were used in treating printcloth woven of yarn containing polyester blended with cotton in the proportions specified in Table X. The treated fabrics were machine washed and tumble dried, and after a specified number of such laundering cycles, were subjected to the Quinn test for antibacterial activity, using *Staphylococcus epidermidis* as the inoculant. The results appear in Table X.

Table X

| % Cotton | % Polyester | Percent Decrease in Colony Count | | |
|---|---|---|---|---|
| | | 0 Cycles | 20 Cycles | 50 Cycles |
| 100 | 0 | 100 | 100 | 100 |
| 65 | 35 | 100 | 99 | 39 |
| 50 | 50 | 100 | 65 | 40 |
| 35 | 65 | 100 | 15 | 22 |
| 0 | 100 | 98 | 77 | 69 |

The data show that the treatment was more effective and durable on all-cotton fabric than on all-polyester fabric, but that a considerable antibacterial activity was imparted to all the fabrics treated.

EXAMPLE 10

Application of Zinc Acetate-Hydrogen Peroxide to Paper

To 52.8 parts by weight of water in a flask was added 125 parts of 30% aqueous hydrogen peroxide, 10.5 parts glacial acetic acid and 40.0 parts zinc acetate dihydrate. The flask was then stoppered and mechanically shaken for 15 min. to yield a clear solution. White typewriting paper, 25% bond, was immersed and thoroughly wet in the solution, and was freed of excess liquid by being passed between squeeze rolls of a wringer. The paper was heat-cured in a forced-draft oven for 5 min. at 85° C. It was then rinsed for 5 min. in water, and dried at 85° C. for 5 min. The treated paper contained 0.15% peroxide by titration. In the parallel streak test with *Staphylococcus aureus*, it produced a 0.5 mm zone of bacterial inhibition, whereas untreated paper produced no zone of inhibition.

We claim:

1. A process for rendering cellulosic textiles bacteriostatic, which process comprises:
    (a) immersion of the cellulosic textile in an aqueous treating solution which contains about from 1% to 30% zinc acetate and from 1% to 30% hydrogen peroxide in water, and which, at zinc acetate concentrations of 5% or greater, also contains from 1% to 25% acetic acid to prevent precipitation of peroxide complexes of zinc acetate,
    (b) removal of excess treating solution from the cellulosic textile,
    (c) drying the cellulosic textile to cause deposition of peroxide complexes of zinc acetate on the textile,
    (d) washing the cellulosic textile to remove excess reagents, and
    (e) drying the treated cellulosic textile to remove water.

2. The process of claim 1 where the cellulosic textile is cotton fabric.

3. The process of claim 1 where the cellulosic textile is paper.

4. As a textile material, the cellulosic textile treated by the process of claim 1.

5. As a textile material, cotton fabric treated by the process of claim 1.

6. As a textile material, paper treated by the process of claim 1.

7. A process for preparing durable press cotton fabrics that are bacteriostatic, which process comprises:
    (a) immersion of a cotton fabric in an aqueous treating solution containing a durable press finished reagent selected from the group consisting of dimethylolethyleneurea and dimethyloldihydroxyethyleneurea, and also containing a Lewis acid catalyst,
    (b) drying the fabric,
    (c) heating the fabric to a temperature producing cellulose crosslinking by the durable press reagent,
    (e) washing the fabric,
    (f) drying the fabric,
    (g) immersion of the resulting durable press fabric in an aqueous solution which contains about from 1% to 30% zinc acetate and from 1% to 30% hydrogen peroxide in water, and which, at zinc acetate concentrations of 5% or greater, also contains from 1% to 25% acetic acid to prevent precipitation of peroxide complexes of zinc acetate,
    (h) drying the cellulosic textile to cause deposition of peroxide complexes of zinc acetate on the textile,
    (i) washing the cellulosic textile to remove excess reagents, and
    (j) drying the treated cellulosic textile to remove water.

8. The process of claim 7 where the durable press finishing reagent is dimethylolethyleneurea.

9. The process of claim 7 where the durable press finishing reagent is dimethyloldihydroxyethyleneurea.

10. As a textile material, cotton fabric treated by the process of claim 7.

11. As a textile material, cotton fabric treated by the process of claim 7 where the durable press finishing reagent is dimethylolethyleneurea.

12. As a textile material, cotton fabric treated by the process of claim 7 where the durable press finishing reagent is dimethyloldihydroxyethyleneurea.

13. A process for rendering polyester textiles bacteriostatic, which process comprises:
    (a) immersion of the polyester textile in an aqueous treating solution which contains about from 1% to 30% zinc acetate and from 1% to 30% hydrogen peroxide in water, and which, at zinc acetate concentrations of 5% or greater, also contains from 1% to 25% acetic acid to prevent precipitation of peroxide complexes of zinc acetate,
    (b) removal of excess treating solution from the polyester textile,
    (c) drying the textile to cause deposition of peroxide complexes of zinc acetate on the textile,
    (d) washing the polyester textile to remove excess reagents, and
    (e) drying the treated polyester textile to remove water.

14. As a textile material, the polyester textile treated by the process of claim 13.

15. As a textile material, polyester fabric treated by the process of claim 13.

* * * * *